United States Patent [19]

Wagner et al.

[11] 4,001,290
[45] Jan. 4, 1977

[54] ORGANIC ISOCYANATE COMPOSITIONS AND PRODUCTION THEREOF

[75] Inventors: Kuno Wagner, Leverkusen; Rudolf Braden, Odenthal-Scheuren, both of Germany

[73] Assignee: Bayer Aktiengesellschaft, Leverkusen, Germany

[22] Filed: Mar. 12, 1969

[21] Appl. No.: 806,695

[30] Foreign Application Priority Data

Mar. 15, 1968 Germany .......................... 1668115

[52] U.S. Cl. ............................ 260/453 A; 252/182; 260/2.5 AT; 260/77.5 CH; 260/77.5 AT; 260/453 AB; 260/453 AL; 260/453 AR

[51] Int. Cl.[2] .......... C07C 119/042; C07C 119/045; C07C 119/048

[58] Field of Search .............. 260/453 AR, 453 AL, 260/453 P, 453 AB, 453 A

[56] References Cited
UNITED STATES PATENTS 3,517,039  6/1970  Wagner et al. ................ 260/453 X

OTHER PUBLICATIONS

Houben–Weyl: Methoden der Organishen Chemie, vol. 11/1, p. 600 (1957).
Sabatier et al.: Chemical Abstracts, vol. 1, p. 2689 (1907).

Primary Examiner—Lewis Gotts
Assistant Examiner—Dolph H. Torrence
Attorney, Agent, or Firm—Gene Harsh; Joseph C. Gil

[57] ABSTRACT

Organic isocyanate compositions are prepared by reacting organic polyisocyanates alone or in the presence of other organic compounds which contain reducible functional groups with catalytically activated hydrogen. New N-formyl-N,N'-disubstituted diisocyanato ureas may be prepared by this method. The products of this invention are particularly useful for producing light fast lacquers, coatings, adhesives, telomers and foam plastics.

9 Claims, No Drawings

ORGANIC ISOCYANATE COMPOSITIONS AND PRODUCTION THEREOF

FIELD OF THE INVENTION

This invention relates to organic isocyanate compositions and more particularly to a method for preparing organic isocyanate compositions. Still more particularly the invention relates to the production of new N-formyl-N,N'-disubstituted diisocyanato ureas.

DISCUSSION OF PRIOR ART

It has been heretofore known that the reduction of monoisocyanates produces N-methylsubstituted amines according to the following reaction equation:

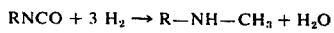

$$RNCO + 3 H_2 \rightarrow R-NH-CH_3 + H_2O$$

and derivatives of formamide are also formed as reduction products; see Houben-Weyl, Methoden der Organischen Chemie, Volume 11/1, page 600. In this reduction process, non-uniform end products are obtained which no longer contain any NCO groups. Also, it has heretofore been well known that polyisocyanates are extremely sensitive to many metals and metal oxides and they often polymerize to form insoluble and cross-linked polyisocyanurates in an uncontrollable and often vigorous reaction with the production of much heat. It was, therefore, not expected that polyisocyanates would be capable of undergoing controlled polyaddition reactions in the presence of very finely divided active metals or metal oxides, such as commercially known hydrogenation catalysts, and in the presence of catalytically activated hydrogen to form polyisocyanates.

OBJECTS

It is, therefore, an object of this invention to provide a process for the production of polyisocyanate reaction products which is devoid of the foregoing problems and disadvantages. A further object of this invention is to provide valuable mono- or polyisocyanates or polyisocyanate mixtures which have a wide range of constitutions and NCO functionalities and which are usually almost or completely inaccessible by other methods. A further object of this invention is to provide a process for the production of reaction products of organic isocyanates with compounds containing groups highly reactive with isocyanate groups under controlled process conditions. A still further object of this invention is to provide a process for the production of novel N-formyl-N,N'-disubstituted diisocyanato ureas. Still another object of this invention is to provide novel N-formyl-N,N'-disubstituted diisocyanato ureas.

SUMMARY OF INVENTION

The foregoing objects and others which will become apparent from the following description are accomplished in accordance with this invention, generally speaking, by providing mono- or polyisocyanates or polyisocyanate mixtures by reacting an organic polyisocyanate alone or in the presence of other organic compounds which also contain reducible groups, such as mono- or dinitriles, mono- or polyketones, hydroxy-containing aldehydes, mono- or polyepoxides, all types of nitro compounds, nitroso compounds, Schiff's bases, ketimines, hydrazones, oximes, aldazines, ketazines or hydrazine derivatives, with catalytically activated hydrogen. In the process of this invention wherein organic compounds which contain reducible functional groups are employed in combination with the organic polyisocyanate reactants, the organic compounds which contain reducible functional groups are converted into compounds which are highly reactive with polyisocyanates and, therefore, as they are formed they react with the polyisocyanates present. More particularly, objects of this invention are accomplished by the production of organic isocyanate compositions by a process wherein an organic polyisocyanate alone or in the presence of other organic compounds which contain reducible functional groups are reacted with hydrogen in the presence of an hydrogenation catalyst using at least one mol of isocyanate and preferably about a 4 to about a 6-fold molar excess of isocyanate per equivalent of the reduced functional groups.

DETAILED DISCLOSURE OF INVENTION

According to the invention, therefore, reactive compounds such as N-formyl compounds, polyamines, polyalcohols, hydrazine derivatives or hydroxylamine derivatives are produced from organic compounds, such as polyisocyanates, and other compounds which contain reducible functional groups, which react as they are formed with those isocyanate groups of the polyisocyanate which have not yet been attacked. Since the compounds produced by reduction are never allowed to accumulate in the reaction medium owing to their reactivity, the process according to the invention provides a practically ideal method of dosing the reactants produced by the reduction reaction. Thus it is possible to produce oligomeric polyisocyanates of all types of different constitutions without the formation of higher molecular weight or cross-linked polyaddition products. The process of this invention, therefore, considerably widens the range of commercially available polyisocyanates which are of particular interest for the production of high grade polyurethane lacquers, coatings, polyurethane elastomers, foam plastics and the like.

To illustrate the process of the invention, the following reaction scheme is given for the case where hexamethylene diisocyanate is used as the polyisocyanate component:

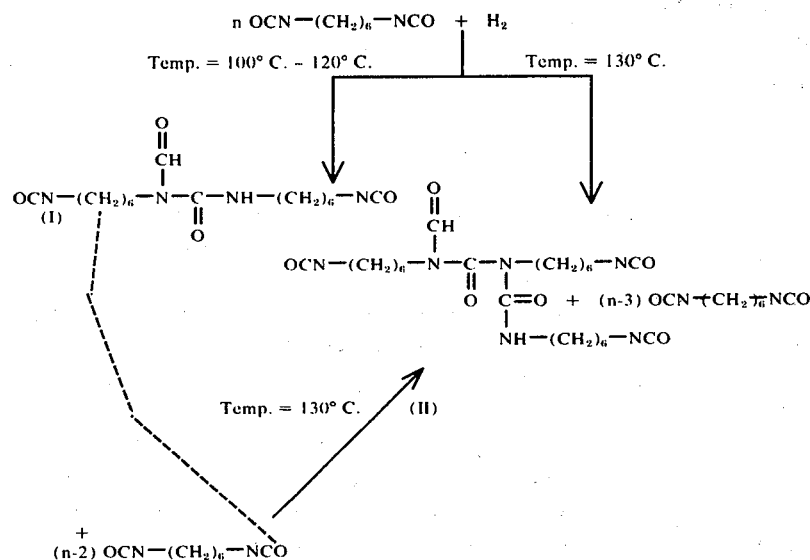

The process according to the invention generally leads to isocyanate mixtures, and the reaction scheme is intended to indicate that the reaction can be controlled by suitable choice of the reaction temperature so that one or the other isocyanate compound will preferentially accumulate in the mixture.

The process of this invention provides a convenient way of producing a group of new N-formyl-N,N'-disubstituted diisocyanate ureas which interalia constitute a preferred embodiment of the invention. Polyisocyanates of this constitution are not obtainable, for example, merely by reacting polyisocyanates with formic acid since formic acid in the presence of polyisocyanates decomposes into carbon monoxide and water, which is the reverse of the reaction in which it is formed, so that polyisocyanates with a biuret structure are obtained owing to the H₂O/NCO reaction. Experience has shown that severe interference of the reaction then occurs. Polyisocyanates of type (I) and (II) in the above reaction scheme are important compounds for the production of air drying polyurethane and polyurea lacquers and coatings owing to the presence of the formamide group in the polyisocyanate molecule; see presence of mono- or dinitriles, that is, compounds in which the reducible functional group is more readily reduced than the NCO group, valuable polyisocyanates are also again obtained, for example, according to the following reaction schemes wherein R may be, for example, any suitable alkyl, cycloalkyl, aralkyl or aryl radical:

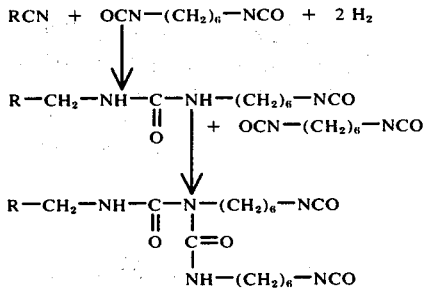

and the following reactions take place where ketimines or di-Schiff's bases are used:

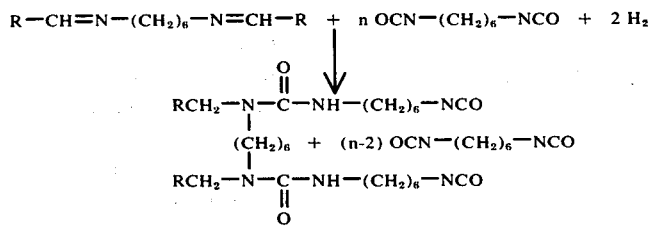

Examples 1 to 3.

If the process according to the invention is carried out in the presence of other organic compounds which contain reducible groups, such as, for example, in the The process according to the invention also provides another possibility for varying the structures produced if nitro compounds of any desired type are included. The reaction is again illustrated below with reference to the scheme in which hexamethylene diisocyanate is given as an example:

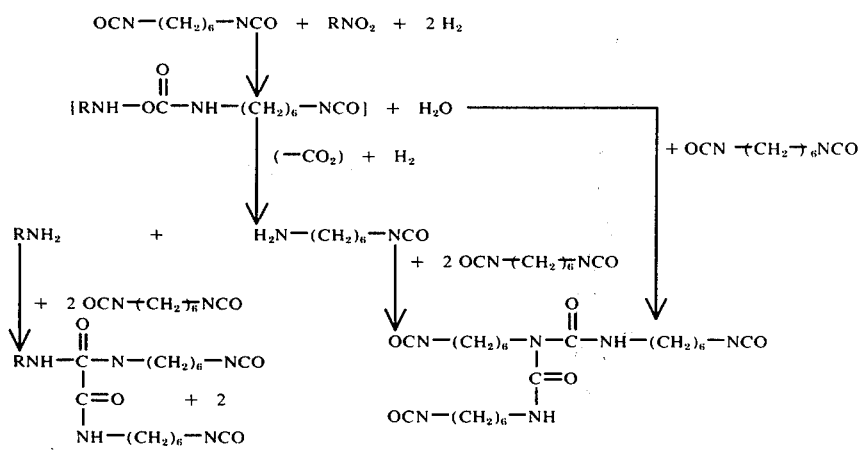

Here again polyisocyanates may be obtained which may consist, for example, of 1 mol of a bifunctional biuret diisocyanate and 2 mols of a biuret triisocyanate, the formation of which can be attributed to the intermediate formation of water in the course of the reduction and to the further reaction of the isocyanatohexylamine formed as a reductive decomposition product, according to the hereinabove reaction scheme.

The constitution and NCO functionality of the end products and their solubility in industrial solvents, their physical drying characteristics and their resistance to heat can be varied as desired in a controlled manner by using different mono- or di-nitro compounds in the process according to the invention. In cases where these compounds are further reacted, for example, to produce cross-linked end products, such as air drying polyurea or polyurethane lacquers, coatings or foam plastics, it is possible, by adjusting the properties of the polyisocyanates, to control the properties of these end products, such as, for example, their elasticity, degree of cross-linking, heat resistance and chemical resistance.

If hydrazine derivatives are used as organic compounds which contain reducible functional groups, the reactions take place, for example, according to the following scheme:

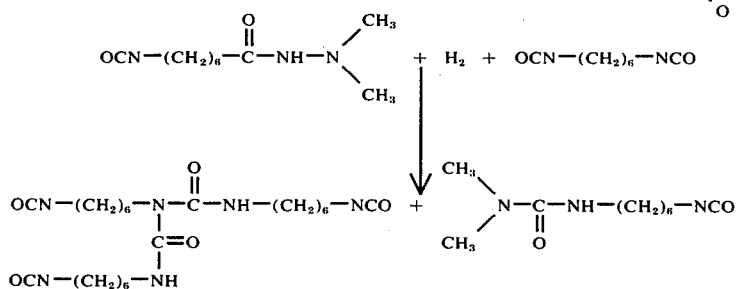

As a result of these reactions, polyisocyanates which have an almost water-clear color and which have excellent heat resistance even at high temperatures can be obtained.

In the process of this invention any suitable known hydrogenation catalysts, such as, for example, Raney nickel, Uruschibara nickel, nickel boride or nickel on any suitable carriers, cobalt on any suitable carriers, Raney cobalt, copper chromites, noble metal hydrogenation catalysts such as, for example, platinum, palladium, rhodium and ruthenium metals or their oxides on carriers and the like may be used for carrying out the process according to the invention. Mixed catalysts can also be used if desired.

It may be advantageous to modify the catalyst used by employing any suitable activating or inactivating additives such as, for example, KCN, KSCN, iodine or activated charcoals and the like. It is especially advantageous to use nickel as the hydrogenation catalyst, especially nickel on kieselguhr as a carrier. Raney nickel or Raney cobalt are also advantageous as catalysts especially when aliphatic, cycloaliphatic or araliphatic polyisocyanates are used as the starting materials.

The following Table shows the classes of reducible functional groups and organic compounds having said reducible functional groups which may be used according to the process of this invention and which are converted by reduction into compounds which are highly reactive with isocyanates.

Table 1

Reducible functional groups $$-C\overset{H}{\underset{O}{\diagdown\!\!\!\!\diagup}} \quad -\overset{|}{\underset{|}{C}}-NO_2 \quad -C\equiv N$$

$$-\overset{|}{\underset{|}{C}}-NO \quad \diagup\!\!\!\!C=NH$$

Table 1-continued

Reducible functional groups $$-\underset{|}{\overset{|}{C}}-NH-OH \qquad \overset{\displaystyle >}{\phantom{.}}C=NR$$

$$\overset{\displaystyle \backslash}{\underset{\displaystyle /}{C}}=O \qquad -\underset{|}{\overset{|}{C}}-N=N-\underset{|}{\overset{|}{C}}- \qquad \overset{\displaystyle >}{\phantom{.}}C=NOH$$

$$-N=C=N- \qquad \overset{\displaystyle >}{\phantom{.}}C=N-N\overset{\displaystyle <}{\phantom{.}}$$

$$-CH-\!\!-\!\!-CH_2 \qquad \overset{\displaystyle >}{\phantom{.}}C=N-N=C\overset{\displaystyle <}{\phantom{.}}$$
$$\phantom{xx}\backslash\;/$$
$$\phantom{xxxx}O$$

$$-\underset{|}{\overset{|}{C}}-NH-NH-\underset{|}{\overset{|}{C}}- \qquad -\underset{|}{\overset{|}{C}}N_3$$

$$-\underset{|}{\overset{|}{C}}-NH-NH_2 \qquad -\underset{|}{\overset{|}{C}}-NCO$$

$$-\underset{|}{\overset{|}{C}}-NH-NO$$

$$-\underset{|}{\overset{|}{C}}-NH-NO_2$$

These functional groups may be attached to any suitable aliphatic, cycloaliphatic, araliphatic, aromatic or heterocyclic radicals. If reducible compounds which have N-N bonds are used, these are usually split by the reduction and react as amines with the polyisocyanate reactants used.

The following are given as representative individual examples of organic compounds with reducible groups. It will be quite clear, however, that any other suitable compounds containing such reducible groups may also be employed within the scope of the invention.

1. Carbonyl compounds:

Diacetyl, acetylacetone, 2-hydroxy-2-methylpentanone, pentaldol, mono-, di- and tri-methylolacetone, dimethylol cyclohexanone, camphor, methyl isopropyl ketone, salicylic aldehyde, p-hydroxybenzophenone and the like.

2. Expoxides:

Glycidic aldehyde, glycidic alcohol, allyl glycidic ether, the diglycidic ether of 1,4-butenediol, diepoxides of bisphenol A or aniline or polyphenols with epichlorohydrin, glycidyl methacrylate and the like.

3. Compounds which contain reducible nitrogen-oxygen, nitrogen-nitrogen or carbon-nitrogen bonds:

Nitrosobenzene, phenylhydroxylamine, azobenzene, diphenylcarbodiimide, phenylhydrazine, hydrazodicarboxylic acid diethyl ester, the ethyl ester of carbazic acid; semicarbazide polyisocyanates described in copending U.S. patent application Ser. No. 760,085 filed Sept. 16, 1968 such as, for example, those produced from 2 mols of cyclohexanone and 1 mol of a diamine, such as, for example, hexamethylene diamine or tetramethylene diamine and the like; Schiff's bases such as, for example, those which can be obtained in a known manner from 2 mols of isobutyraldehyde and 2 mols of isobutyraldehyde and 2 mols of an aliphatic diamine, such as, for example, hexamethylene diamine, tetramethylene diamine or decamethylene diamine and the like; ketazines, such as, for example, those produced from 2 mols of cyclohexanone and 1 mol of hydrazine and the like; aldazines, such as, for example, those produced from 2 mols of benzaldehyde and 1 mol of hydrazine and the like; carbazic acid esters, such as, for example, those produced from 1,1-asymmetrically substituted hydrazines, such as dimethyl hydrazine or cyclohexanone oxime and the like.

4. Nitro compounds:

Nitromethane, nitroethane, nitrocyclohexane, nitrobenzene, 4-nitrotoluene, 4,4'-dinitrodiphenylsulphone, 4-nitroso-diphenylamine, 2,4-dinitrotoluene and chloro-, alkyl- and alkoxy substituted aromatic nitro compounds, and the like.

5. Mono- and poly-nitriles:

Acetonitrile, hydroxyacetonitrile, propionitrile, ethyl cyano acetate, acetone cyanhydrin, butyric acid nitrile, acrylic acid nitrile, crotonic acid nitrile, cyclohexyl cyanide, tetrahydrobenzonitrile, benzyl cyanide, benzonitrile, isonicotinic acid nitrile, 3-aminobenzonitrile, 2-chlorobenzonitrile, 4-chloro-2-nitrobenzonitrile, 4-nitrophenyl acetonitrile; cyanoethylation products of acrylonitrile and mono- or polyamines, CH-acidic compounds and mono- or polyols, such as, for example, the addition products derived from acrylonitrile and methyl- and dimethylamine, ethyl- and diethylamine, cyclohexylamine, 1,4-diaminobutane, 1,6-diaminohexane, 2,2-dimethylpropanediol-(1,3), sorbitol, malonic acid esters, acetone, methyl ethyl ketone, ethyl acetoacetate, nitromethane, cyclohexanone, lactams such as $\epsilon$-caprolactam and pyrrolidone, hydrazine, succinimide, benzenesulphamide, butadiene sulphone and the like. Dinitriles, such as malonic acid dinitrile, succinic acid dinitrile, adipic acid dinitrile, 2-butene-1,4-dinitrile, m- and p-xylylene-dinitriles, phthalic acid dinitrile and isophthalic acid dinitrile and the like and chlorosubstituted aromatic mono- and di-nitriles and the like are also suitable.

6. NCO Compounds:

In the process according to this invention, any suitable polyisocyanates may be used either alone or in admixture. Any such suitable aliphatic, cycloaliphatic, aromatic or araliphatic polyisocyanate may be employed. Preferably the organic polyisocyanates are aliphatic, cycloaliphatic, aromatic or araliphatic hydrocarbon polyisocyanates. As examples of such suitable organic polyisocyanates there may be mentioned the following: ethylene diisocyanate, propylene diisocyanate, 1,4-tetramethylene diisocyanate, 1,5-pentamethylene diisocyanate, 1,6-hexamethylene diisocyanate, 2,4,4-trimethyl-1,6diisocyanatohexane, 1,9-nonane diisocyanate, 1,10-decamethylene diisocyanate, 1,12-dodecamethylene diisocyanate, 1,2-cyclohexane diisocyanate, 1,4-cyclohexane diisocyanate, 1,2-cyclobutane diisocyanate, isophorone diisocyanate, dicyclohexyl-4,4'-diisocyanate, 1-methyl-2,4-diisocyanato-cyclohexane, 1-methyl-2,6-diisocyanatocyclohexane, m- and p-xylylene diisocyanates and isomeric mixtures of these two diisocyanates, 1,3- and 1,4-phenylene diisocyanates, 1,3,5-triisopropyl-2,4-diisocyanatobenzene, 4-chloro-1,3-phenylene diisocyanate, 2,4- and 2,6-toluylene diisocyanates and any mixtures of these isomers such as an 80/20 mixture of 2,4- and 2,6-toluylene diisocyanate, 4,4'-, 2,4'- and 2,2'-diphenylmethane diisocyanates and any isomeric mixtures of these diphenylmethane diisocyanates, 4,4'-diphenylene diisocyanate, 4,4'-diphenylsulphone diisocyanate, 4,4'-diphenylether diisocyanate, 4,4'-dicyclohexylmethane diisocyanate, 4,4'-diphenylpropane diisocyanate, 1,5-naphthalene diisocyanate, 1,3,5-benzene trisocyanate, 4,4',4''-triphenylmethane triisocyanate and the like. Other suitable polyisocyanates are disclosed in U.S. Pat. Nos. 3,282,215 and 3,412,050. Especially preferred are 4,4'-diphenylmethane diisocyanate and its mixtures with the 2,4'- and 2,2'-diphenylmethane diisocyanate isomers.

If particularly high grade, light fast products are to be produced, it is preferable to use aliphatic, cycloaliphatic or araliphatic polyisocyanates or isocyanate-containing polymers of these polyisocyanates. The following are examples of such preferred aliphatic, cycloaliphatic and araliphatic polyisocyanates: 1,4-tetramethylene diisocyanate, 1,5-pentamethylene diisocyanate, 1,6-hexamethylene diisocyanate, 2,4,4-trimethyl-1,6-diisocyanatohexane, 1,12-dodecamethylene diisocyanate, 1,2-diisocyanatocyclobutane, dicyclohexyl-4,4'-diisocyanate, dicyclohexylmethane-4,4'-diisocyanate, p- and m-xylylene diisocyanates, 1-methyl-2,4-diisocyanatocyclohexane and isophorone diisocyanate.

For certain purposes, such as, for example, to improve the flow of lacquers and to promote their rapid physical drying, it is often advantageous to use triisocyanates or to include these in quantities of from about 10% by weight to about 40% by weight, based on the diisocyanate used. Triisocyanates of this kind are, for example, biuret triisocyanates which may be prepared from diisocyanates, such as, for example, according to the process disclosed in German Patent Specification 1,101,394, an addition product of diisocyanates with low molecular weight trifunctional polyols, such as, for example, addition products of 3 mols of diisocyanate with 1 mol of trimethylolpropane, glycerol, aminoethanol, diethanolamine, triethanolamine and the like. Polymers and copolymers of the said diisocyanates with aromatic diisocyanates, such as, for example, those which contain about 40% of 1,6-hexamethylene diisocyanate and about 60% of 2,4-toluene diisocyanate, that is, a polyisocyanate which may contain several isocyanurate rings, are also suitable. Polymers such as those prepared according to the process of copending U.S. patent application Ser. No. 760,085, filed Sept. 16, 1968, may also be used.

Any suitable higher molecular weight polyisocyanates may also be used according to the process of the invention as the starting polyisocyanates, such as, for example, those which can be obtained as a diisocyanate polyaddition product, for example, from hydroxyl-containing and/or amino-containing polyesters, polyethers, polythioethers, polycarbonates, polyacetals, polysiloxanes and the like and excess polyisocyanates.

The following are given as examples of aromatic polyisocyanates which may be used according to the invention: 2,4- and 2,6-toluylene diisocyanates and their chlorination products and isomeric mixtures, such as, for example, an 80/20 mixture of 2,4- and 2,6-toluylene diisocyanate, p- and m-phenylene diisocyanates, ethylated 2,4- and 2,6-toluylene diisocyanates, triisopropylbenzene diisocyanates, 4,4'-diphenylmethane diisocyanate and isomers and ethylated derivatives thereof, 1,5-naphthylene diisocyanate and the like and their masked derivatives such as uretdiones, compounds which split off phenols and compounds which split off imidazole and caprolactam, which compounds liberate the isocyanate groups as a result of the heat generated by the reaction.

Polyisocyanates which are especially preferred for use in the process of the invention are 1,6-hexamethylene diisocyanate, m-xylylene diisocyanate, isophorone diisocyanate and 1-methyl-cyclohexane-2,4- and 1-methylcyclohexane-2,6-diisocyanates and any mixtures of these isomers. It is especially preferred and advantageous to use as the additional organic compounds with reducible functional groups in addition to the polyisocyanates, cyanoethylated lactams and diepoxides derived from 4,4'-dihydroxy-diphenyldimethylmethane.

The process according to the invention is carried out in a manner similar to the procedures customarily and usually employed for catalytic hydrogenations. Thus, for example, the reduction may be carried out intermittently or continuously at hydrogen pressures of up to about 250 atmospheres or higher, preferably at about 90 to about 150 atmospheres. The process may, however, be carried out without the use of pressure, but it is preferred that the process according to the invention be carried out under a pressure of hydrogen.

In this process, the polyisocyanate present, based on 1 mol of hydrogen consumed (which is equivalent to one reduced functional group) should be present in a quantity of at least about one mol and preferably in an amount of about a 4 to 6 fold molar excess.

Elevated temperatures are generally employed such as, for example, temperatures of from about 80° C. to about 200° C. or higher, preferably from about 90° C. to about 150° C., although in certain cases, such as, for example, where it is not necessary to obtain maximum yields, temperatures of from about 60° C. to about 80° C. may also be employed.

The process according to the invention may be carried out either in the presence of, or without, solvents. However, in order to preserve the activity of the hydrogenation catalysts, it is preferred to carry out the reduction reactions in inert organic solvents generally employed in hydrogenation reactions, such as, for example, in dioxane, tetrahydrofuran, butyl acetate, amyl acetate, cyclohexane, benzene, toluene, xylene, chlorobenzene, glycol monomethylether acetate, N-methylpyrrolidone and the like.

In cases where the formation of monoisocyanates is desired in the production of the products of this process, the ratio of diisocyanate to the functional groups which are to be reduced should be such that at least one mol of an organic diisocyanate will enter into reaction per equivalent of reduced functional group. If on the other hand it is desired to obtain polyisocyanates as products of the process, which in fact is a preferred embodiment of the invention, then at least 2 mols and preferably about a 4 to about a 6-fold molar excess of the polyisocyanate should be used, based on the equivalent of the reduced functional groups.

In many of those cases in which the subsequent use of the product renders the removal of any monomeric starting polyisocyanate unnecessary, such as, for example, in the case of N,N',N''-tris-(isocyanatohexyl)-biuret and other biuret types from polyfunctional isocyanates and polyamines or in the case of addition products of 3 mols of a bi-functional diisocyanate with 1 mol of a trifunctional polyol, the working up process of the products can be simple, for example, the products may be simply filtered off from the catalyst and any solvent used in the process may then be distilled off if necessary. If desired, after removal of the catalyst the products of the process of the invention may be used directly in the solvent used for hydrogenation, such as, for example, in a 50% to 75% solution, for the production of air drying polyurea lacquers or polyurethane lacquers in a manner known to those skilled in the art.

If, on the other hand, it is desired to free the products of the process from any monomeric starting polyisocyanates present, the products are removed by any suitable separation procedure, such as, for example, by thin layer evaporation, for example, at 0.2 mm. Hg. and 120° C. to 180° C. or by extraction, such as, for example, with ligroin, cyclohexane and the like or by any other suitable separation procedure.

The process according to the invention makes it possible, for instance, to synthesize biuret polyisocyanates which are difficult or impossible to produce by heretofore known processes. Thus, for example, tetramethylene diamine or hexamethylene diamine cannot be used satisfactorily for the synthesis of the corresponding low molecular weight biuret polyisocyanates since it is technically impossible to keep the amounts of polyamine added to the polyisocyanate sufficiently small that further reaction with the polyisocyanates remains at the stage of formation of low molecular weight easily soluble biuret polyisocyanates. By the process according to this invention, however, this reaction can be carried out without difficulty since the dosing of the polyamine occurs in an ideal manner in minimum quantities due to the relatively slow hydrogenation of the dinitrile used, so that the reaction can be arrested at the diisocyanatodiurea stage. Easily soluble reaction products are thus easily obtained by this method, and these products yield clear solutions which, because of their high fluidity can be easily removed from monomeric polyisocyanates by thin layer evaporation.

Additionally, the process of this invention can be employed for the synthesis of new N-formyl-N'-isocyanatoalkyl-, isocyanatocycloalkyl-, isocyanatoaralkyl- and isocyanatoaryl- ureas and for their conversion into biuret polyisocyanates which contain formamide groups. Preferred isocyanate compounds of the invention are those having the formula

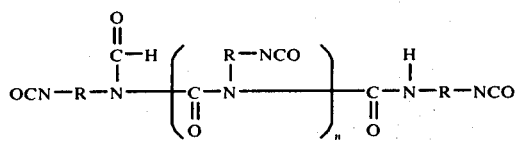

wherein n is 0 or a positive integer from 1 to 3 and R is the organic radical remaining after removal of the isocyanato groups from an organic polyisocyanate.

Further reaction of this group of products provided by the process of this invention leads to usable polyurea lacquers and polyurethane lacquers as shown in the Examples.

The production of polyisocyanates which contains urethane groups may also be carried out very advantageously according to the invention since the alcohols or polyalcohols formed as the intermediate products in the reduction are captured as they are formed so that there is always only small quantities of polyols available for reacting with the excess polyisocyanates.

UTILITY

The products of the process, which are usually easily soluble, are suitable for numerous purposes, such as, for example, for the production of light fast polyurethane and polyurea lacquers, coatings, adhesives, such as, for example, for composition glass and the like, and for the production of all types of foam plastics, if desired in admixture with known polyisocyanates according to procedures known to those skilled in the art. Furthermore, the aliphatic, cycloaliphatic and araliphatic products of the process, if reacted further in accordance with the procedure of copending U.S. patent application Ser. No. 773,964, filed Nov. 7, 1968, constitute useful telogens for the production of light fast, NCO-containing telomers of polyisocyanates and ethylenically unsaturated monomers.

EXAMPLES

The invention is further illustrated but is not intended to be limited by the following examples in which all parts and percentages are by weight unless otherwise specified.

EXAMPLE 1

About 10 parts of a hydrogenation catalyst which consists of finely divided nickel on kieselguhr as a carrier are added to about 972 parts of 1,6-hexamethylene diisocyanate and about 600 parts by volume of anhydrous toluene in a 3-liter autoclave of VA steel equipped with a stirrer. When the autoclave has been purged several times with nitrogen, it is charged with hydrogen and the pressure is adjusted to about 100 atmospheres at a temperature of about 120° C. Hydrogenation is carried out for about 5 hours at this temperature, the pressure dropping to about 78 atmospheres during the process. During this reaction time, about 1 NCO equivalent is reduced to isocyanato-hexylformamide by 1 mol of hydrogen, and this formamide reacts with the excess hexamethylene diisocyanate to form N-formyl-bis-(isocyanatohexyl)urea. When the pressure in the autoclave has been released, the catalyst is filtered off, the toluene is removed under vacuum by means of a water pump and the solution of the reaction product is freed from excess hexamethylene diisocyanate by thin layer distillation at about 0.2 mm Hg and about 140° C. About 321 parts of a pale yellow diisocyanate which has an NCO content of about 24.8% are obtained. According to an osmotic molecular weight determination, this has an average molecular weight of 340. According to the percent NCO content, elementary analysis and IR spectroscopic data, the polyisocyanate consists of about 85% of N-formyl-bis-(isocyanatohexyl) urea and about 15 percent of higher homologues of N-formyl-tris-(isocyanatohexyl)-biuret.

When about 0.2 percent of zinc octoate are added to about 50% solutions of the monomer-free polyisocyanate in ethyl acetate and the solutions are painted on glass, wood or sheet steel, clear, light fast, highly elastic, air drying lacquer films are obtained which have dried sufficiently to be non-sticky after about 4 hours and have become insoluble after about 24 hours.

EXAMPLE 2

The same procedure as in Example 1 is employed but the hydrogenation catalyst is replaced by about 10 parts of Raney cobalt. The product is worked up as described in Example 1. The thin liquid polyisocyanate obtained is slightly colored blue by traces of cobalt in colloidal solution. Yield: about 330 parts; NCO content: about 22.5%.

EXAMPLE 3

About 840 parts of 1,6-hexamethylene diisocyanate, about 600 parts by volume of anhydrous toluene and about 10 parts of finely divided nickel on kieselguhr as a carrier are reacted under the hydrogenating conditions described in Example 1 but the temperature is adjusted to about 140° C. and the hydrogen pressure to about 120 atmospheres. Reaction time is about 7 hours. During this time, about 2 NCO equivalents have been reduced with about 2 mols of hydrogen to isocyanatohexyl formamide which reacts with excess 1,6-hexamethylene diisocyanate to form N-formyl-bis-(isocyanatohexyl)-urea. This is worked up as described in Example 1. Yield: about 639 parts; NCO content: about 17.1%. Highly elastic, light fast, air drying lacquers can be produced from the polyisocyanate as described in Example 1. When a polyester of trimethylolpropane and phthalic acid having an OH content of about 8.5% and the polyisocyanate (75% solution in ethyl acetate and methyl isobutylketone) is painted on glass and cross-linked using an NCO/OH equivalent ratio of 1, a light fast, chemically resistant polyurethane lacquer is obtained.

EXAMPLE 4

The same procedure is employed as used in Example 1 but the hexamethylene diisocyanate is replaced by about 880 parts of isophorone diisocyanate (A) and about 940 parts of m-xylylene diisocyanate (B). The product is worked up as described in Example 1. The monomeric diisocyanate is purified by thin layer evaporation at about 145° C. and about 0.2 mm Hg. In the case of (A), a polyisocyanate which has an NCO content of about 18.2% is obtained. Yield: about 380 parts. In the case of (B), a polyisocyanate which has an NCO content of about 21.8% is obtained in a yield of about 310 parts. The polyisocyanates obtained consist of more than 75% of N-formylated urea diisocyanates of isophorone- or m-xylylene-diisocyanate.

EXAMPLE 5

The same procedure as used in Example 1 is employed but about 696 parts of an isomeric mixture of about 80 parts of 2,4-toluene diisocyanate and about 20 parts of 2,6-toluene diisoccyanate are employed. Hydrogenation is carried out at a temperature of about 150° C. and a hydrogen pressure of about 120 atmospheres and the hydrogenation catalyst and toluene are removed after a reaction time of about 5 hours as is described in Example 1. A solution which has an NCO content of about 36% is obtained. This solution contains about 50% of isomeric N-formylated urea diisocyanate derivatives in unreacted monomeric diisocyanate and this product can be used directly for the production of foam plastics without further purification.

EXAMPLE 6

The same procedure as described in Example 5 is employed but about 680 parts of a commercial polyisocyanate isomer mixture which consists of about 30% of 4,4'-diphenylmethane diisocyanate and tri- and tetrafunctional polyisocyanates such as those which are obtained in the phosgenation of acid condensed aniline-formaldehyde resins are used. After removal of the hydrogenation catalyst by filtration, the toluene is removed under vacuum by means of a water pump. A liquid, highly fluid polyisocyanate mixture which has an NCO content of about 25% and which can be used for the production of hard foam plastics which exhibit an improved heat resistance is obtained.

EXAMPLE 7

About 972 parts of 1,6-hexamethylene diisocyanate, about 43.2 parts of adipic acid dinitrile and about 600 parts by volume of anhydrous toluene are hydrogenated by the procedure given in Example 1 with about 10 parts of a catalyst which consists of finely divided nickel on kieselguhr as a carrier, using the hydrogen pressure given in Example 1. The product is worked up as described in Example 1 and about 385 parts of a polyisocyanate mixture which consists of about 60% of N-formyl-bis-(isocyanatohexyl)urea and about 40% of a biuret polyisocyanate which contains nitrile groups and which has been produced by the reaction of hexamethylene diisocyanate with partially hydrogenated adipic acid dinitrile are obtained; NCO content about 20.5%.

When about 50% solutions of this polyisocyanate in ethyl acetate, which contain about 0.2% of tin (II)-octoate and about 0.1% of dimethyl benzylamine, is painted on glass, elastic films which are distinguished from the films produced from the polyisocyanates of Example 1 by increased bond strength on glass supports are produced.

EXAMPLE 8

About 660 parts of isophorone diisocyanate, about 31 parts of succinic acid dinitrile and about 600 parts by volume of anhydrous toluene are reacted in the presence of catalytically activated hydrogen by the procedure of Example 7. The product is worked up as in Example 1 and about 390 parts by weight of a polyisocyanate which still contains free nitrile groups and which has an NCO content of about 21.5% are obtained. About 75% solutions of this polyisocyanate in a mixture of xylene and ethyl glycol acetate (1:1), which solutions contain 0.2% of stannous octoate as catalyst, produce after painting on glass, clear, high gloss films which have dried sufficiently to be non-sticky after about 7 hours and are cross-linked after about 24 hours.

EXAMPLE 9

A mixture of about 82 parts of acetonitrile and about 336 parts of 1,6-hexamethylene diisocyanate in about 1500 parts by volume of toluene is reacted with catalytically activated hydrogen as described in Example 1 and worked up in the usual manner. A reaction product which consists of about 70% of the addition product of 1 mol of 1,6-hexamethylene diisocyanate and 1 mol of ethylamine (monoisocyanate) and about 30% of N-formyl-bis-(isocyanatohexyl)urea is obtained; NCO content about 21.5%.

EXAMPLE 10

About 522 parts by weight of an isomeric mixture of about 80 parts of 2,4-toluene diisocyanate and 20 parts of 2,6-toluene diisocyanate, about 25 parts of nitrobenzene and about 600 parts by volume of toluene are treated and worked up as described in Example 1. A polyisocyanate mixture which consists substantially of 2 mols of tris-(1-methyl-2-isocyanatophenyl)biuret and 1 mol of N-phenyl-N',N''-bis-(1-methyl-2-isocyanatophenyl)biuret is obtained in a yield of about 480 parts; NCO content about 22.9%.

EXAMPLE 11

About 840 parts of 1,6-hexamethylene diisocyanate, about 36.9 parts of nitrobenzene and about 600 parts by volume of toluene are reacted according to the procedure of Example 1 for about 5 hours under the hydrogenation conditions given in Example 1, using about 10 parts by weight of a catalyst which consists of finely divided nickel on kieselguhr. After removal of excess hexamethylene diisocyanate in a thin layer evaporator at about 140° C. and about 0.2 mm Hg, an almost water-clear, highly fluid polyisocyanate mixture is obtained in a yield of about 580 parts, having an NCO content of about 22.5%. The polyisocyanate obtained consists substantially of a di- and tri-isocyanate and has approximately the composition of a mixture of 2 mols of N,N',N''-tris-(isocyanatohexyl)biuret and 1 mol of N-phenyl-N',N''-bis-(isocyanatohexyl)biuret.

EXAMPLE 12

About 840 parts of 1,6-hexamethylene diisocyanate, about 100 parts of a ketimine formed from 2 mols of cyclohexanone and 1 mol of 1,6-hexamethylene diamine, and about 600 parts by volume of toluene are reacted together under the hydrogenating conditions given in Example 11. After about 5 hours, the product is worked up as described in Example 11. Yield: about 633 parts; NCO content: about 15.8%. The polyisocyanate obtained is readily soluble, such as, for example, in ethyl acetate, butyl acetate and xylene, methyl ethyl ketone and ethyl glycol acetate and can be emulsified in petroleum hydrocarbons, and consists substantially of the bis-isocyanatohexyl-diurea of N,N'-dicyclohexyl-hexamethylene diamine.

If this diisocyanate is added in portions of about 15% to lacquer solutions which contain about 75% of N,N',N''-tris-(isocyanatohexyl)-biuret and the solutions are painted on glass, one obtains, after hardening of these solutions, lacquer films which have an increased resistance to tearing and are more flexible than lacquer films based on N,N',N''-tris-(isocyanatohexyl)-biuret.

EXAMPLE 13

About 840 parts of hexamethylene diisocyanate, about 112 parts of the di-Schiff's base formed from 2 mols of isobutyraldehyde and 1 mol of 1,6-hexamethylene diamine and about 600 parts by volume of anhydrous toluene are hydrogenated as described in Example 12 for about 5 hours at about 120° C. and under a hydrogen pressure of about 120 atmospheres. The product is then worked up as described in Example 11. Yield: about 694 parts; NCO content: about 15.4%.

The polyisocyanate obtained, which consists substantially of a readily soluble substituted diisocyanato diurea derivative, is easily soluble in vinyl monomers such as methyl acrylate, ethyl acrylate, butyl acrylate or methyl methacrylate and can be used in the method described in copending U.S. patent application Ser. No. 773,964 filed Nov. 7, 1968 as active telogens for numerous vinyl monomers such as acrylates and methacrylates and the like.

EXAMPLE 14

About 504 parts of 1,6-hexamethylene diisocyanate, about 130 parts of cyanoethylated caprolactam and about 600 parts by volume of anhydrous toluene are hydrogenated and worked up as described in Example 13. Yield: about 385 parts. The almost water-clear polyisocyanate obtained consists of a mixture of about 38% of N-formyl-N,N'-bis-(isocyanatohexyl)urea and about 62% of the addition product of 1 mol of aminoethyl caprolactam to 2 mols of 1,6-hexamethylene diisocyanate; NCO content is about 16.9%.

EXAMPLE 15

About 504 parts of 1,6-hexamethylene diisocyanate, about 116 parts of cyanoethylated pyrrolidone and 600 parts by volume of anhydrous toluene are hydrogenated and worked up as described in Example 13. Yield: about 330 parts of polyisocyanate; NCO content: about 17.9%. If about 50% solutions of the monomer-free polyisocyanate in ethyl acetate are treated with about 0.2% of stannous octoate and the solutions are painted on glass, wood or sheet steel, clear, lightfast, air drying one component lacquers are obtained which have dried sufficiently to become non-sticky after about 4 hours and have become insoluble after about 24 hours.

EXAMPLE 16

About 522 parts of 2,4-toluene diisocyanate, 200 parts of a bis-epoxide of 4,4'-dihydroxy-diphenyl-dimethylmethane and epichlorohydrin with an epoxide equivalent of about 200 and about 700 parts by volume of anhydrous toluene are hydrogenated as described in Example 13. In this process, the epoxide rings are split open by the reduction and polyisocyanates which contain urethane groups are formed. Working up and purification of the monomeric diisocyanate is carried out as described in Example 13. Yield: about 320 parts; NCO content: about 10.8%. If about 50% solutions of the monomer-free polyisocyanate in ethyl acetate are treated with about 0.2% of tin dibutyl dilaurate and the solutions are painted on glass, air-drying one component lacquers which have dried to the non-sticky stage in about 6 hours and have become insoluble in about 24 hours are obtained.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention.

What is claimed is:
1. N,-formyl-N,N'-disubstituted diisocyanato urea having the formula:

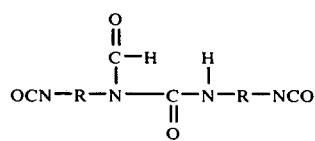

wherein R is the organic radical remaining after the removal of the isocyanato groups from an organic diisocyanate selected from the group consisting of aliphatic, cycloaliphatic, aromatic or araliphatic diisocyanates.

2. A process for the production of the N-formyl-N,N'-disubstituted diisocyanato urea of claim 1 comprising reacting at a temperature of from about 60° C. to about 200° C. an organic diisocyanate selected from the group consisting of aliphatic, cycloaliphatic, aromatic or araliphatic diisocyanates with hydrogen in the presence of a hydrogenation catalyst from about 1 to about 6 mols of diisocyanate being present for each mol of hydrogen consumed.

3. The process of claim 2 wherein the polyisocyanate is hexamethylene diisocyanate.

4. The process of claim 2 wherein the polyisocyanate is m-xylene diisocyanate.

5. The process of claim 2 wherein the polyisocyanate is a toluylene diisocyanate.

6. The process of claim 5 wherein the toluylene diisocyanate is an isomeric mixture of 2,4- and 2,6-toluylene diisocyanate.

7. The process of claim 2 wherein the polyisocyanate is isophorone diisocyanate.

8. The process of claim 2 wherein the reaction is carried out in the presence of an inert solvent.

9. The process of claim 2 wherein the hydrogenation catalyst is nickel on kieselguhr.

* * * * *